US011246955B2

(12) United States Patent
Woodbridge

(10) Patent No.: US 11,246,955 B2
(45) Date of Patent: Feb. 15, 2022

(54) METHOD AND SYSTEM FOR GENERATING NON-THERMAL PLASMA

(71) Applicant: Terrance Woodbridge, Cary, NC (US)

(72) Inventor: Terrance Woodbridge, Cary, NC (US)

(73) Assignee: PHOENIXAIRE, LLC, McLean, VA (US)

( * ) Notice: Subject to any disclaimer, the term of this patent is extended or adjusted under 35 U.S.C. 154(b) by 187 days.

(21) Appl. No.: 16/173,677

(22) Filed: Oct. 29, 2018

(65) Prior Publication Data

US 2020/0129652 A1   Apr. 30, 2020

(51) Int. Cl.
*A61L 9/22* (2006.01)
*H05H 1/48* (2006.01)
*H01T 23/00* (2006.01)
*H05H 1/24* (2006.01)

(52) U.S. Cl.
CPC ............... *A61L 9/22* (2013.01); *H01T 23/00* (2013.01); *H05H 1/48* (2013.01); *H05H 1/471* (2021.05); *H05H 2245/36* (2021.05)

(58) Field of Classification Search
CPC .... A61L 9/22; H05H 1/48; H05H 2245/1225; H05H 2001/483; H05H 2240/20; H05H 2001/481; H01T 23/00
See application file for complete search history.

(56) References Cited

U.S. PATENT DOCUMENTS

| 906,468 A | 12/1908 | Steynis |
| 1,157,859 A | 10/1915 | Freet |
| 1,454,219 A | 5/1923 | Goedicke |

(Continued)

FOREIGN PATENT DOCUMENTS

| CN | 1312448 | 4/2007 |
| DE | 1923081 | 11/1970 |

(Continued)

OTHER PUBLICATIONS

International Search Report and Written Opinion for PCT/US2019/058317, dated Jan. 9, 2020.

(Continued)

*Primary Examiner* — Sean E Conley
*Assistant Examiner* — Brendan A Hensel
(74) *Attorney, Agent, or Firm* — Wiley Rein LLP

(57) ABSTRACT

Disclosed herein are apparatuses and methods for generating non-thermal plasma which can form reactive oxygen species (ROS), such as those used to neutralize bacteria and other pathogens in the air and surrounding area. Also disclosed are apparatuses and methods for neutralizing bacteria and other pathogens using ROS generated through the use of non-thermal plasma. Also disclosed are apparatuses and methods for generating ROS. Also disclosed are apparatuses and methods for treating air and nearby surfaces. Also disclosed herein are apparatuses for generating non-thermal plasma, and which can monitor and analyze the operational characteristics of a plasma field generated by the aforementioned devices and/or the electrical consumption characteristics of the power supply being used to generate the plasma field, which analyzed characteristics can be used to trigger an alarm to indicate that the device is not functioning optimally or as otherwise expected.

28 Claims, 7 Drawing Sheets

(56) References Cited

U.S. PATENT DOCUMENTS

| | | | |
|---|---|---|---|
| 1,505,669 A | 8/1924 | Quain | |
| 2,162,809 A | 6/1939 | Groak et al. | |
| 2,687,781 A | 8/1954 | Sens | |
| 2,778,443 A | 1/1957 | Yereance | |
| 3,730,874 A | 5/1973 | Trub | |
| 3,833,492 A | 9/1974 | Bollyky | |
| 3,921,002 A | 11/1975 | Williams et al. | |
| 3,967,131 A | 6/1976 | Slipiec | |
| 4,025,441 A | 5/1977 | Tabata et al. | |
| 4,048,668 A | 9/1977 | Von Bargen et al. | |
| 4,049,552 A | 9/1977 | Arff | |
| 4,051,045 A | 9/1977 | Yamamoto et al. | |
| 4,079,260 A | 3/1978 | Dmitriev et al. | |
| 4,101,783 A | 7/1978 | Hutter | |
| 4,123,664 A | 10/1978 | Yamamura et al. | |
| 4,128,768 A | 12/1978 | Yamamoto et al. | |
| 4,159,971 A | 7/1979 | Gneupel | |
| 4,210,949 A * | 7/1980 | Masuda | B03C 3/38 361/226 |
| 4,216,096 A | 8/1980 | Pare et al. | |
| 4,234,800 A | 11/1980 | Kenly et al. | |
| 4,323,379 A | 4/1982 | Shearin | |
| 4,383,976 A | 5/1983 | Notaro | |
| 4,411,756 A | 10/1983 | Bennett et al. | |
| 4,417,966 A | 11/1983 | Krauss et al. | |
| 4,461,744 A | 7/1984 | Emi et al. | |
| 4,504,446 A | 3/1985 | Kunicki et al. | |
| 4,614,573 A | 9/1986 | Masuda | |
| 4,640,782 A | 2/1987 | Burleson | |
| 4,650,573 A | 3/1987 | Nathanson | |
| 4,656,010 A | 4/1987 | Leitzke et al. | |
| 4,690,803 A | 9/1987 | Hirth | |
| 4,696,800 A | 9/1987 | Sasaki et al. | |
| 4,725,412 A | 2/1988 | Ito | |
| 4,764,349 A | 8/1988 | Arff et al. | |
| 4,877,588 A | 10/1989 | Ditzler et al. | |
| 4,878,642 A | 11/1989 | Kirby, Jr. | |
| 4,886,645 A | 12/1989 | Fischer et al. | |
| 4,960,569 A | 10/1990 | Fovell et al. | |
| 4,981,656 A | 1/1991 | Leitzke | |
| 5,004,587 A | 4/1991 | Tacchi | |
| 5,008,087 A | 4/1991 | Batchelor | |
| 5,015,442 A | 5/1991 | Hirai | |
| 5,034,198 A | 7/1991 | Kaiga et al. | |
| 5,093,087 A | 3/1992 | Freeman | |
| 5,124,132 A | 6/1992 | Francis, Jr. et al. | |
| 5,145,653 A | 9/1992 | Fischer et al. | |
| 5,268,151 A | 12/1993 | Reed et al. | |
| 5,387,842 A | 2/1995 | Roth et al. | |
| 5,411,713 A | 5/1995 | Iwanaga | |
| 5,508,008 A | 4/1996 | Wasser | |
| 5,523,057 A | 6/1996 | Mazzilli | |
| 5,579,705 A * | 12/1996 | Suzuki | F27D 3/1545 110/185 |
| 5,833,740 A | 11/1998 | Brais | |
| 5,961,920 A | 10/1999 | Söremark | |
| 5,989,303 A | 11/1999 | Hodge | |
| 5,997,428 A | 12/1999 | Kagata et al. | |
| 6,039,214 A | 3/2000 | Hewett | |
| 6,066,348 A | 5/2000 | Yuan et al. | |
| 6,165,423 A | 12/2000 | Crosbie | |
| 6,228,149 B1 | 5/2001 | Alenichev et al. | |
| 6,280,691 B1 | 8/2001 | Homeyer et al. | |
| 6,358,478 B1 | 3/2002 | Söremark | |
| 6,481,219 B2 | 11/2002 | Palermo | |
| 6,503,547 B1 | 1/2003 | Lima | |
| 6,528,023 B2 | 3/2003 | Fleischer | |
| 6,613,277 B1 | 9/2003 | Monagan | |
| 6,620,385 B2 | 9/2003 | Fujii | |
| 6,630,105 B1 | 10/2003 | O'Neill et al. | |
| 6,811,757 B2 * | 11/2004 | Niv | H05H 1/2406 204/164 |
| 6,866,828 B2 | 3/2005 | Segawa et al. | |
| 6,893,610 B1 | 5/2005 | Barnes | |
| 6,991,768 B2 | 1/2006 | Keras et al. | |
| 7,192,553 B2 | 3/2007 | Crowe et al. | |
| 7,651,555 B2 | 1/2010 | Roseberry et al. | |
| 10,111,977 B1 * | 10/2018 | Woodbridge | H05H 1/48 |
| 10,729,801 B2 * | 8/2020 | Woodbridge | A61L 9/22 |
| 2003/0066285 A1 | 4/2003 | Raybone et al. | |
| 2003/0072675 A1 | 4/2003 | Takeda et al. | |
| 2003/0106788 A1 * | 6/2003 | Babko-Malyi | F01N 3/0892 204/164 |
| 2003/0121770 A1 | 7/2003 | McNulty, Jr. | |
| 2004/0135379 A1 | 7/2004 | Meier et al. | |
| 2004/0175318 A1 | 9/2004 | Segawa et al. | |
| 2004/0184972 A1 | 9/2004 | Kelly et al. | |
| 2004/0262241 A1 | 12/2004 | Socha | |
| 2005/0023128 A1 | 2/2005 | Keras et al. | |
| 2005/0169821 A1 | 8/2005 | Boschert et al. | |
| 2005/0186108 A1 | 8/2005 | Fields | |
| 2006/0233660 A1 | 10/2006 | Furuhashi et al. | |
| 2007/0041882 A1 | 2/2007 | Roseberry et al. | |
| 2007/0176562 A1 * | 8/2007 | Takikawa | H05H 1/48 315/111.21 |
| 2008/0035472 A1 | 2/2008 | Lepage | |
| 2008/0193326 A1 | 8/2008 | Mole | |
| 2008/0199351 A1 | 8/2008 | Woodbridge | |
| 2010/0254868 A1 | 10/2010 | Obee et al. | |
| 2011/0030320 A1 | 2/2011 | Blumenstock et al. | |
| 2011/0280764 A1 | 11/2011 | Benson et al. | |
| 2012/0063959 A1 | 3/2012 | Woodbridge et al. | |
| 2013/0057151 A1 | 3/2013 | Curry et al. | |
| 2014/0373817 A1 | 12/2014 | Waddell et al. | |
| 2015/0085421 A1 * | 3/2015 | Ploeg | H05K 7/20 361/231 |
| 2015/0145173 A1 * | 5/2015 | Hachinohe | B22F 3/02 264/408 |
| 2015/0248989 A1 * | 9/2015 | Ezaki | A61L 9/22 313/230 |
| 2016/0074805 A1 * | 3/2016 | Liu | B01J 19/243 422/170 |
| 2016/0135273 A1 * | 5/2016 | Gefter | H05F 1/00 361/213 |

FOREIGN PATENT DOCUMENTS

| | | |
|---|---|---|
| EP | 0560690 | 9/1993 |
| EP | 1125588 | 8/2001 |
| EP | 1508289 | 2/2005 |
| EP | 1968653 | 2/2013 |
| JP | 10511572 | 11/1998 |
| JP | 10314289 | 12/1998 |
| JP | 2001221565 | 8/2001 |
| JP | 2005095649 | 4/2005 |
| WO | 96/20017 | 7/1996 |
| WO | 00/78670 | 12/2000 |
| WO | 03/038351 | 5/2003 |
| WO | 03/092752 | 11/2003 |
| WO | 03/101498 | 12/2003 |
| WO | 04/062800 | 7/2004 |
| WO | 2007064368 | 6/2007 |

OTHER PUBLICATIONS

Marsden, James L., Evaluation of AirOcare Reaction Chamber and Reactive Oxygen Species for Reducing Methicillin Resistant *Staphylococcus Aureus*, Acinetobacter Baumannii and Listeria Monocytogenes on Stainless Steel, Plastic and Polyethylene Surfaces (Executive Summary), K-State Food Science Institute, Kansas State University, Manhattan, KS 66506, Retrieved Feb. 19, 2016.

Falkenberg, R., AirOcare Technology, Creating a Safe Food Environment by Eliminating Influenza A, MRSA, Norovirus , and Rhinovirus on Various Inoculated Surfaces, FSPT, 6 pgs, Retrieved Feb. 19, 2016.

International Preliminary Report on Patentability for PCT/US06/28734 dated Feb. 8, 2012.

Office action for U.S. Appl. No. 11/289,363 dated Jun. 22, 2010.

European Search Opinion dated Oct. 4, 2010.

Supplemental European Search Report, dated Oct. 4, 2010.

(56) References Cited

OTHER PUBLICATIONS

Office action for U.S. Appl. No. 11/289,363, dated Jun. 17, 2009.
Fantech: FR Series Fans—Specifications, Retrieved Jun. 14, 2005 from http://www.fantech.net/fr2.htm.
English abstract of JP Publication No. 2005095649, dated Apr. 13, 2012.
English translation of JP Publication No. 10-314289, dated Mar. 23, 2012.
English abstract of CN Publication No. 1312448, dated Aug. 26, 2011.
English abstract of EP Publication No. 1125588, dated Apr. 1, 2011.
English abstract of EP Publication No. 1508289, dated Feb. 20, 2007.

* cited by examiner

METHOD AND SYSTEM FOR GENERATING NON-THERMAL PLASMA

CROSS-REFERENCE TO RELATED APPLICATIONS

This application is related to U.S. nonprovisional patent application Ser. No. 14/922,975, filed Oct. 26, 2015, pending, entitled "Method and System for Generating Non-Thermal Plasma" (which application included a claim of priority to U.S. provisional application No. 62/187,410, filed 1 Jul. 2015, entitled "System to Reduce the Pathogens, Volatile Organic Compounds and Viruses in Air"). Each of these applications is hereby incorporated by reference as though fully set forth herein.

FIELD OF THE INVENTION

The present invention relates to apparatuses and methods for generating non-thermal plasma which can form reactive oxygen species, which in turn, can be used to neutralize bacteria and other pathogens in the air and surrounding area. The present invention also relates to apparatuses and methods for neutralizing bacteria and other pathogens using reactive oxygen species generated through the use of non-thermal plasma. The present invention also relates to a monitor that analyzes operational characteristics of a plasma field generated by the aforementioned devices and/or the electrical consumption characteristics of the power supply being used to generate the plasma field, which analyzed characteristics can be used to trigger an alarm to indicate that the device is not functioning optimally or as otherwise expected.

BACKGROUND OF THE INVENTION

Today's high-efficiency particulate arrestance (HEPA) filters do not have the capability to deal with all aspects of indoor air pollution. Although HEPA filters may be effective at filtering out as much as 99.97% of air borne particles that have a size of 0.3 μm or larger, they are not always effective at treating or removing airborne contaminants made up of microorganisms, viruses, and bacteria smaller than 0.3 μm, all of which are potentially harmful. The inventions disclosed herein, through new devices for and new methods of producing Reactive Oxygen Species ("ROS"), have the ability to treat and remove airborne contaminants using processes that produce a non-thermal plasma field from ambient air within a reaction chamber.

One of ordinary skill in the art would understand "non-thermal plasma" to refer to plasma that is not in thermodynamic equilibrium. In particular, as used herein, "non-thermal plasma" refers to plasma that is produced by a process that does not involve the use or generation of substantial heat; in other words, the temperature of the fluid used to generate the plasma (e.g., ambient air) is not substantially increased during the process of generating plasma. It is known in the art that non-thermal plasma contains reactive forms of oxygen, i.e., ROS, that have a much higher reactivity than oxygen in the form of stable oxygen molecules, which include atomic oxygen, singlet oxygen, hydrogen peroxide, superoxide anion, tri-atomic oxygen and hydroxyl radicals. It is known that ROS can react with particles as small as and smaller than about 0.3 microns. The antimicrobial properties of ROS in the air and on surfaces is known, and the mechanisms by which ROS inactivate bacteria has been studied. See, e.g., Suresh G. Joshi, M. Cooper, A. Yost, M. Paff, U. K. Ercan, G. Fridman, G. Friedman, A. Fridman, and A. D. Brooks, "Nonthermal dielectric-barrier discharge plasma-induced inactivation involves oxidative DNA damage and membrane lipid peroxidation in Escherichia coli," Antimicrobial Agents Chemotherapy, vol. 55, no. 3, pp. 1053-1062, March 2011 (which article is incorporated by reference in its entirety into this application). It is understood, for example, that the different ROS attach themselves to the surfaces of contaminants and other pathogens at bond sites to create strong oxidizing radicals. These radicals draw out the hydrogen that is present in these contaminants and other pathogens, breaking down the surface membranes and rendering them inactive (in other words, neutralizing the contaminants and pathogens). The end result may be that the hydroxide and hydrogen radicals combine and form water, and the contaminants and pathogens are inactivated and neutralized. Viruses, however, are bundles of nucleic acid surrounded by a protein bases capsid. When viruses are exposed to ROS both the capsid and viral RNA can be destroyed.

Furthermore, the ROS generated in the non-thermal plasma fields described herein can also breakdown Volatile Organic Compounds (VOC). When carbon based VOCs (alcohols, aldehydes, and ketones) pass through the non-thermal plasma, the covalent bonds in the molecules can be broken, which can also produce carbon dioxide and/or oxygen.

Unlike many other low energy technologies, the present invention avoids producing toxic intermediates. The inventions disclosed herein can be used for food preservation, in medical applications, and other industries in which airborne contaminants can be problematic.

BRIEF SUMMARY OF THE INVENTION

One aspect of the inventions disclosed is to provide a system and method for utilizing ambient air to generate ROS to neutralize pathogens, viruses and volatile organic compounds from the air for the purpose of treating the air and the surrounding areas.

Disclosed herein is an air treatment apparatus having an intake portion, an output portion, and a reaction chamber located between the intake portion and output portion. The reaction chamber includes an anode rail assembly and a cathode rail. The anode rail assembly may include a helical anode rail made of a first conductive material and having a shape of a helix along a longitudinal axis, and a plurality of discharge anode elements spaced along the helix. Each of the plurality of discharge anode elements has a proximal end and a distal end, such that the proximal ends of the discharge anode elements are secured to the helical anode rail, and each of the plurality of discharge anode elements is electrically coupled to each other and to the helical anode rail. The plurality of discharge elements may face the central inner axis of the helical anode rail. The cathode rail may be made of a second conductive material, and may be positioned such that it is substantially along the inner longitudinal axis of the helical anode rail, such that the cathode rail may be opposite and facing the plurality of discharge anode elements. The helical anode rail assembly and the cathode rail are located relative to each other so as to form a hollow cylindrical space that separates the cathode rail from the plurality of discharge anode elements such that the discharge anode elements do not cross the cylindrical space. The air treatment apparatus may also include an intake blower located in the intake portion, wherein the intake blower is configured to draw air into the reaction chamber. The air treatment apparatus also includes an alternating current power supply capable of delivering sufficient energy to generate a non-thermal plasma field in the space between the helical anode rail assembly and the cathode rail. The air treatment apparatus may optionally include a sensor (e.g., configured to monitor tri-atomic oxygen), and preferably, the sensor may be located externally to the apparatus. In one embodiment the air treatment apparatus may utilize the same material for the first conductive material and the second conductive material, though in another embodiment, the first conductive material may be different from the second conductive material. For example, the first conductive material and second conductive material may each be selected from the group consisting of silver, copper, gold, aluminum, zinc, brass, steel and alloys of the foregoing elements. Optionally, at least a portion of an outer surface of the distal ends of the discharge anode elements may be textured to facilitate formation of plasma, including for example, one or more of grooves, etchings, ridges, dimplings, and pittings. The air treatment apparatus may have a cathode rail which has an outer surface, at least a portion of which surface is textured, such that the textured surface faces the distal ends of the discharge anode elements. The textured surface of the cathode rail may include, for example, comprises one or more of grooves, etchings, ridges, dimplings, and pittings. In addition, the air treatment may include one or more filters, either on the air intake portion or the air output portion. Preferably, the cathode rail may be cylindrical. Preferably, each of the plurality of discharge anode elements on the helical anode rail is spaced a fixed distance from a neighboring discharge anode. More preferably, the spacing is fixed between approximately 1/8 inch and approximately 3 inches. One of skill in the art would appreciate that using a greater number of discharge anode elements may require increasing the wattage of the power supply being used.

Also disclosed is an ambient air treatment device, comprising: a reaction chamber having an anode assembly and a cathode rail spaced opposite the anode assembly, an airflow input on a first side of the anode assembly and the cathode rail, and an airflow output on a second side of the anode assembly and the cathode rail; and a power supply coupled to the anode assembly and to the cathode rail capable of generating a plasma field between the anode assembly and the cathode rail. The anode assembly may include a common electrical bus and a plurality of discharge anode elements extending outward from the common electrical bus, said discharge anode elements having a textured surface on a distal end for discharging electrical current. The cathode rail may include one or more conductive elements placed in electrical contact with each other so as to form an electrically-conductive, elongated cathode having an outer surface, wherein at least a portion of the outer face contains a textured surface for receiving electrical current. The elongated cathode may be a cylindrical rod. The ambient air treatment device can operate using different power supplies in order to create different volumes of ROS. For example, the ambient air treatment device can operate using a power supply outputting greater than about 1,000 VAC at a frequency of about 60 Hz. Alternatively, the ambient air treatment device can operate using a power supply outputting greater than about 1,000 VAC at a frequency of greater than about 1,000 Hz. Alternatively, the ambient air treatment device can operate using a power supply outputting greater than about 2,000 VAC at a frequency of greater than about 10,000 Hz. Each of the anode assembly and the cathode rail may be made using a conductive material comprising at least one of silver, copper, gold, aluminum, zinc, brass, and steel. For example, the anode assembly may be made using a first conductive material selected from: silver, copper, gold, aluminum, zinc, brass, steel, and stainless steel, and the cathode rail is made using a second conductive material, different from the first conductive material, selected from: silver, copper, gold, aluminum, zinc, brass, steel, and stainless steel. The ambient air treatment device can include an elongated helical anode assembly having a distance of D as measured on a longitudinal axis, and a cathode rail that is elongated, is substantially cylindrical, is positioned along the longitudinal axis of the helical anode assembly, and has a distance of about the same or less than D, wherein the plurality of discharge anode elements extend towards the cathode rail but remain spaced from the cathode rail to permit the creation of a plasma field in a cylindrical space between the helical anode assembly and the centrally-located cathode rail. The textured surface on the distal end of each of the plurality of discharge anodes, as well as the textured surface on the outer surface of the cathode rail, may each be formed using a variety of formations to facilitate formation of plasma, including for example, one or more of: a cross-hatch pattern, grooves, etchings, ridges, dimplings, and pittings. The ambient air treatment device may optionally include a blower to generate an air flow across the plasma field during operation of the ambient air treatment device.

A method of generating a non-drifting plasma field is also disclosed. The method may include the steps of: drawing air into a reaction chamber, wherein the reaction chamber having an anode rail assembly, a cathode rail, and a gap located between the anode rail assembly and the cathode rail; supplying energy to the anode rail assembly to generate a plasma field in the gap between the anode rail assembly and the cathode rail; and causing the air to flow through the plasma field created in the reaction chamber. The anode rail assembly may include a helical anode rail made of a first conductive material, in a shape of a helix having a longitudinal axis, and a plurality of discharge anode elements arranged on the helical anode rail. The cathode rail may be a rod located along the longitudinal axis of the helix. The gap between the anode rail assembly and the cathode rail is cylindrical and the cathode rail is positioned along the longitudinal axis of the helical anode rail, said gap separating the cathode rail from the plurality of discharge anode elements such that the discharge anode elements do not cross the cylindrical gap. Each of the plurality of discharge anode elements has a proximal end and a distal end, and the proximal ends may be secured to the helical anode rail, and each of the plurality of discharge anode elements may be electrically coupled to each other and to the helical anode rail. The method may be performed using discharge anode elements having a distal end in the form of a pointed tip, and optionally, the distal ends of the discharge anode elements have a rough surface to assist with discharging electrical current. The cathode rail is made of a second conductive material. The method may generate a plasma field using power characterized by greater than about 1,000 VAC at a frequency of about 60 Hz. Alternatively, the method may generate a plasma field using greater than about 1,000 VAC at a frequency of greater than about 1,000 Hz. Alternatively, the method may generate a plasma field using greater than about 2,000 VAC at a frequency of greater than about 10,000 Hz. The method may be used to create a fan-shaped non-thermal plasma field that emanates from one or more of the plurality of discharge anode elements towards the cathode rail. Preferably, the energy is used to create a plasma field that is substantially homogenous throughout the gap.

An ambient air treatment device capable of operating in at least two modes is also disclosed. The ambient air treatment device includes a reaction chamber having: a first anode assembly and a first cathode rail, wherein the first anode assembly has a first helical anode rail and a first plurality of discharge anode elements extending inwardly from the first helical anode rail toward the first cathode rail which is centrally located within the first helical anode rail; a second anode assembly and a second cathode rail, wherein the second anode assembly has a second helical anode rail and a second plurality of discharge anode elements extending inwardly from the second helical anode rail toward the second cathode rail which is centrally located within the second helical anode rail; an airflow input on a first side of the first anode assembly, the first cathode rail, the second anode assembly, and the second cathode rail; and an airflow output on a second side of the first anode assembly, the first cathode rail, the second anode assembly, and the second cathode rail. In addition to the reaction chamber, the ambient air treatment device includes: a first alternating current power supply electrically coupled to the first anode assembly and to the first cathode rail capable of generating a first plasma field in a cylindrical space between the first anode assembly and the first cathode rail; a second alternating current power supply electrically coupled to the second anode assembly and to the second cathode rail capable of generating a second plasma field in a cylindrical space between the second anode assembly and the second cathode rail; and a control switch. The control switch is configured to permit the ambient air treatment device to operate in at least two modes, including a first mode that uses the first alternating current power supply to generate a first plasma field and a second mode that uses the second alternating current power supply to generate a second plasma field. Each of the first cathode rail and the second cathode rail may include one or more conductive elements placed in electrical contact with each other so as to form an electrically-conductive, elongated cathode having an outer surface, wherein at least a portion of the outer surface contains a textured surface for assisting in the generation of plasma. The first anode assembly and said first cathode rail may be positioned in spaced relationship, with the first cathode rail being positioned along the central longitudinal axis of the first helical anode rail, and the second anode assembly and said second cathode rail are positioned in spaced relationship, with the second cathode rail being positioned along the central longitudinal axis of the second helical anode rail. Each of the first plurality of discharge anode elements for each of the first anode assembly and the second anode assembly may include a textured surface on a distal end for assisting in the generation of plasma. The first and second alternating current power supplies preferably differ in both the magnitude and frequency of the power source being used to generate plasma. For example, the ambient air treatment device may have a first power supply that operates using greater than about 1,000 VAC at a frequency of about 60 Hz, and may have a second power supply may use greater than about 1,000 VAC at a frequency of greater than about 1,000 Hz. Of course, the second power supply may use other power characteristics as well, including for example a second power supply that operates using greater than about 2,000 VAC at a frequency of greater than about 10,000 Hz. Each of the first and second anode assemblies and each of the first and second cathodes rail may be made out of a conductive material comprising at least one of silver, copper, gold, aluminum, zinc, brass, and steel. For example, each of the first and second anode assemblies may be made using a first conductive material selected from: silver, copper, gold, aluminum, zinc, brass, steel, and stainless steel, and each of the first and second cathode rails may be made using a second conductive material, different from the first conductive material, selected from: silver, copper, gold, aluminum, zinc, brass, steel, and stainless steel. The first anode assembly may optionally be an elongated helix having a longitudinal distance of D1, and the first cathode rail may be an elongated rod, substantially cylindrical and having a distance of less than or about the same as D1. The second anode assembly may optionally be an elongated helix having a longitudinal distance of D2, and the second cathode rail may be an elongated rod, substantially cylindrical and having a distance of less than or about the same as D2. The first plurality of discharge anode elements may extend inwardly toward the first cathode rail, and yet remain spaced from the first cathode rail to permit the creation of a first plasma field in the hollow, cylindrical gap there between. Similarly, the second plurality of discharge anode elements may extend inwardly toward the second cathode rail and yet remain spaced from the second cathode rail to permit the creation of a second plasma field in the cylindrical gap there between. The ambient air treatment device may, further comprise a blower to generate an airflow across at least the first plasma field during operation of the ambient air treatment device. The blower can also be used to generate an airflow across the first and second plasma fields during operation of the ambient air treatment device. The blower may optionally have at least two speeds, whereby the air treatment device can operate the blower at a lower speed when generating plasma in the first mode of operation, or can operate the blower at a higher speed when generating plasma in the second mode of operation. The textured surface on the distal end of each of the plurality of discharge anodes may each be formed using a variety of formations to facilitate formation of plasma, including for example, one or more of: a cross-hatch pattern, grooves, etchings, ridges, dimplings, and pittings. Similarly, the textured surfaces on the outer surface of the cathode rails may be formed using a variety of formations to facilitate formation of plasma, including for example, one or more of: a cross-hatch pattern, grooves, etchings, ridges, dimplings, and pittings. The first anode assembly and second anode assembly may be aligned along a common axis and spaced sufficiently to provide electrical isolation from each other during operation. Similarly, the first cathode rail and the second cathode rail may be aligned along a common axis and spaced sufficiently to provide electrical isolation from each other during operation. The control switch can be configured to permit the ambient air treatment device to operate in a first mode using the first power supply to generate a first reactive oxygen species having a first set of characteristics and to permit the ambient air treatment device to operate in a second mode using the second power supply to generate a second reactive oxygen species having a second set of characteristics, different from the first set of characteristics. For example, the first mode may generate a first volume of ROS which have longer-half lives when compared to the second mode which may generate a smaller volume of ROS with longer half-lives. The ambient air treatment device may utilize power supplies that vary in terms of voltage magnitude and frequency. For example, the ambient air treatment device may use a first power supply that generates plasma using greater than about 5,000 VAC at a frequency of about 60 Hz, and the second power supply may generate plasma using greater than about 5,000 VAC at a frequency of greater than about 10,000 Hz. Alternatively, the ambient air treatment device may use a first power supply that generates plasma using greater than about 2,000 VAC at a frequency of about 60 Hz, and wherein the second power generates plasma using greater than about 1,000 VAC and a frequency of greater than about 1,000 Hz.

Optionally, the control switch can be configured to permit the ambient air treatment device to operate in at least a third mode that uses the first power supply to generate a first plasma field while simultaneously using the second power supply to generate a second plasma field.

Also disclosed is an air treatment apparatus comprising: an intake portion and an output portion; a reaction chamber located between the intake portion and output portion, wherein the reaction chamber includes an anode rail assembly and a cathode rail assembly; an intake blower located in the intake portion, wherein the intake blower is configured to draw air into the reaction chamber; and power supply circuitry capable of delivering sufficient energy to generate a plasma field in the space between the anode rail assembly and the cathode rail assembly. The anode rail assembly may include a helical anode rail made of a conductive material and having a longitudinal axis; and a plurality of discharge anode elements, each of which elements has a proximal end and a distal end, with the proximal ends of the discharge anode elements being secured to the helical anode rail, and with each of the discharge anode elements being electrically coupled to each other and to the helical anode rail. The cathode rail assembly may include a cathode rail made of a conductive material and having a longitudinal axis; and a plurality of cathode elements, each of which elements has a proximal end and a distal end, with the proximal ends of the cathode elements being attached to and protruding from the cathode rail, and with each of the plurality of cathode elements being electrically coupled to each other and to the cathode rail. Preferably, the cathode rail is substantially co-located along the longitudinal axis of the helical anode rail, and the anode rail assembly and the cathode rail assembly are spaced relative to each other so as to form a space between them, such that the space has a central longitudinal axis and further separates the plurality of cathode elements from the plurality of discharge anode elements such that the discharge anode elements are on one side and do not cross the central longitudinal axis of the space and the plurality of cathode elements are on the opposite side of and do not cross the central longitudinal axis of the space. The air treatment apparatus may optionally include a sensor to monitor tri-atomic oxygen. In one embodiment, the sensor is located externally to the apparatus and wirelessly communicates with the air treatment apparatus. While the anode rail assembly and the cathode rail assembly may be made of the same conductive material, they can also be formed using different conductive materials. For example, the anode rail assembly and the cathode rail assembly may be made of conductive materials selected from the group consisting of silver, copper, gold, aluminum, zinc, brass, steel and alloys of the foregoing elements. Optionally, at least a portion of an outer surface of the distal ends of each of the plurality of discharge anode elements and of each of the plurality of cathode elements is textured to facilitate formation of plasma. Optionally, the plurality of cathode elements may be spaced such that each of the cathode elements is equally distant from the two closest discharge anode elements to facilitate the generation of a plasma field in the space between the anode rail assembly and the cathode rail assembly. The power supply may generate plasma using a variety of voltage levels and frequencies. For example, the power supply circuitry may generate plasma using greater than about 1,000 VAC at a frequency of about 60 Hz. Alternatively, the power supply circuitry may generate plasma using greater than about 1,000 VAC at a frequency of greater than about 1,000 Hz. Alternatively, the power supply circuitry may generate plasma using greater than about 2,000 VAC at a frequency of greater than about 10,000 Hz.

Also disclosed herein is a method of generating a plasma field comprising the steps of: drawing air into a reaction chamber having an anode rail assembly, a cathode rail assembly and a gap there between; supplying energy to at least the anode rail assembly to generate a plasma field in the gap between the anode rail assembly and the cathode rail assembly; and causing the air to flow through the plasma field created in the reaction chamber. The anode rail assembly may include: a helical anode rail made of a conductive material and having a longitudinal axis; and a plurality of discharge anode elements; wherein each of the plurality of discharge anode elements has a proximal end and a distal end, the proximal ends of the discharge anode elements are secured to the helical anode rail, and each of the plurality of discharge anode elements are electrically coupled to each other and to the helical anode rail. The cathode rail assembly may include: a cathode rail made of a conductive material and having a longitudinal axis; and a plurality of cathode elements extending from the cathode rail; wherein each of the plurality of cathode elements has a proximal end and a distal end, the proximal ends of the cathode elements are attached to the cathode rail, and each of the plurality of cathode elements are electrically coupled to each other and to the cathode rail. The cathode rail may be substantially coaxial to the helical anode rail; and the anode rail assembly and the cathode rail assembly may be spaced relative to each other so as to form a hollow, cylindrical gap between them. The gap has a central longitudinal axis and further separates the plurality of cathode elements from the plurality of discharge anode elements such that the discharge anode elements are on one side and do not cross the central longitudinal axis of the gap and the plurality of cathode elements are on the other side and do not cross the central longitudinal axis of the gap. The distal ends of each of the discharge anode elements and of each of the cathode elements may comprise a pointed tip, and optionally, the distal ends of each of the discharge anode elements and of each of the cathode elements have a rough surface to assist with discharging electrical current. The step of supplying energy may be met by supplying energy using greater than about 1,000 VAC at a frequency of about 60 Hz. Alternatively, the step of supplying energy may be supplying energy using greater than about 1,000 VAC at a frequency of greater than about 1,000 Hz. Alternatively, the step of supplying energy may be supplying energy using greater than about 5,000 VAC at a frequency of greater than about 10,000 Hz.

Yet another method of generating non-thermal plasma is disclosed, which includes the steps of: using a first power supply to create plasma in a first plasma field in a reaction chamber wherein the plasma created by the first power supply includes a first volume of reactive oxygen species having a half-life of less than about 10 seconds and includes no more than a second volume of a reactive oxygen species having a half-life of greater than about 1 minute; using a second power supply to create plasma in a second plasma field in the reaction chamber wherein the plasma created by the second power supply includes less than the first volume of reactive oxygen species having a half-life of less than about 10 seconds and includes more than the second volume of a reactive oxygen species having a half-life of greater than about 1 minute. The method may include operating the first power supply to generate plasma while the second power supply is not being used to generate plasma. Alternatively, the method may include operating the second power supply to generate plasma while the first power supply is not being used to generate plasma. Alternatively, the method may include operating the first power supply to generate plasma while simultaneously operating the second power supply to generate plasma. The method may include using the first power supply to generate plasma using energy at greater than about 1,000 VAC at a frequency of about 60 Hz. Alternatively, the method may include using the second power supply to generate plasma using energy at a voltage of about 1,000 VAC or greater and at a frequency of about 1,000 Hz or greater.

Yet another device for generating non-thermal plasma is disclosed, which device has at least two modes of operation. The multi-mode device includes a reaction chamber having: a first reactor and a first power supply to create plasma in a first plasma field, wherein the plasma created by the first power supply includes a first volume of reactive oxygen species having a half-life of less than about 10 seconds and includes no more than a second volume of a reactive oxygen species having a half-life of greater than about 1 minute; and a second reactor and a second power supply to create plasma in a second plasma field, wherein the plasma created by the second power supply includes less than the first volume of reactive oxygen species having a half-life of less than about 10 seconds and includes more than the second volume of a reactive oxygen species having a half-life of greater than about 1 minute. Power supplies having at least one of different voltage magnitudes and frequencies are used. For example, the first power supply can generate plasma using energy at greater than about 1,000 VAC at a frequency of about 60 Hz, and the second power supply can generate plasma using energy having a voltage of about or greater than 1,000 VAC and a frequency of about or greater than 1,000 Hz. Alternatively, the second power supply can generate plasma using energy having a voltage of about or greater than 10,000 VAC and a frequency of about or greater than 10,000 Hz.

Also disclosed herein is a performance monitor that can be incorporated into the devices described above. The performance monitor includes at least one of: a) one or more sensors (e.g., light sensors) that monitor the optical characteristics of a plasma field that is generated in the space between the anode rail assembly and the cathode rail; and b) a power supply sensor that analyzes the electrical consumption characteristics of the power supply being used to generate the plasma field. The performance monitor may include an optical receiver that analyzes the optical characteristics of the generated plasma field. The performance monitor may also include a comparator that: a) compares the analyzed optical characteristics of the generated plasma field to a predetermined set of optical characteristics; and/or b) compares the analyzed electrical consumption characteristics of the power supply to a predetermined set of electrical consumption characteristics. The comparator can be programed to issue an alarm to indicate that the device is not functioning optimally if either or both of the following conditions are met: a) the analyzed optical characteristics deviates by more than a first predetermined minimum threshold from the predetermined set of optical characteristics; and b) the analyzed electrical consumption characteristics deviates by more than a second predetermined minimum threshold from a predetermined set of electrical consumption characteristics. The first and second predetermined minimum thresholds may be set using a common measurement stick (e.g., 10%) and/or may be set independently using the same or different measurement sticks.

Also disclosed herein is a treatment device that includes: an intake portion; an output portion; a reaction chamber located between the intake portion and output portion, an intake blower located in the intake portion, wherein the intake blower is configured to draw air into the reaction chamber; and an alternating current power supply that delivers sufficient energy to reaction chamber so as to generate a non-thermal plasma field therein. The reaction chamber includes an anode rail assembly and a cathode rail. The anode rail assembly has an anode rail made of a conductive material, and a plurality of discharge anode elements, each of which has a proximal end and a distal end, whereby the proximal ends are secured to the anode rail, and each of the plurality of discharge anode elements is electrically coupled to each other and to the anode rail. The cathode rail is made of a conductive material, and it is spaced relative to the anode rail assembly to form a space that separates the cathode rail from the plurality of discharge anode elements such that the discharge anode elements do not cross the space. The alternating current power supply is coupled to both the anode rail and the cathode rail, wherein the alternating current power supply delivers sufficient energy to generate a non-thermal plasma field in the space between the anode rail assembly and the cathode rail. The reaction chamber also includes a performance monitor that includes at least one of: a) one or more light sensors that monitor the optical characteristics of a plasma field that is generated in the space between the anode rail assembly and the cathode rail; and b) a power supply sensor that analyzes the electrical consumption characteristics of the power supply being used to generate the plasma field. The performance monitor may include an optical receiver that analyzes the optical characteristics of the generated plasma field. The performance monitor also includes a comparator that: a) compares the analyzed optical characteristics of the generated plasma field to a predetermined set of optical characteristics; and/or b) compares the analyzed electrical consumption characteristics of the power supply to a predetermined set of electrical consumption characteristics. The comparator can be programed to issue an alarm when either or both of the following conditions are met: a) the analyzed optical characteristics deviates by more than a first predetermined minimum threshold from the predetermined set of optical characteristics; and b) the analyzed electrical consumption characteristics deviates by more than a second predetermined minimum threshold from a predetermined set of electrical consumption characteristics. Optionally, the anode may be in the shape of a helix, in which case, the space between the helical anode and the cathode may be a hollow, cylindrical space.

Also disclosed herein is an air treatment apparatus having an intake portion, an output portion, and a reaction chamber located between the intake portion and output portion. The reaction chamber includes a first rail assembly and a second rail assembly. The first rail assembly may have a first rail made of a first conductive material and may be shaped to form a helix along a longitudinal axis. The first rail may include a plurality of protruding elements, each of which has a proximal end and a distal end, with the proximal ends of the protruding elements being secured to the first rail. Each of the plurality of protruding elements is electrically coupled to each other and to the first rail. The second rail assembly may have a second rail made of a second conductive material and may be elongated so that it can be positioned along the longitudinal axis of the helical first rail. The first rail assembly and the second rail assembly are located relative to each other so as to form a hollow, cylindrical space that separates the second rail from the plurality of protruding elements of the first rail, such that the protruding elements do not cross the cylindrical space. An intake blower may be located in the intake portion, wherein the intake blower can draw air into the reaction chamber. An alternating current power supply may be coupled to both the first rail and the second rail, such that the alternating current power supply can deliver sufficient energy to generate a non-thermal plasma field in the space between the first rail and the second rail. In one alternative embodiment, the first rail assembly functions as an anode and the second rail assembly functions as a cathode. In another alternative embodiment, the first rail assembly functions as a cathode and the second rail assembly functions as an anode.

DETAILED DESCRIPTION OF THE INVENTION

The present invention provides an apparatus for generating a non-thermal plasma field for generating ROS. The present invention relates to apparatuses and methods for treating air to help neutralize airborne contaminants such as micro-organisms, viruses, and bacteria. The air treatment apparatuses disclosed herein are capable of constantly producing non-thermal plasma discharge by means of a physical array having at least one anode and cathode (at least one of which includes a plurality of extensions) and power supplies that deliver sufficient energy to create a non-thermal plasma field between the anode and cathode. A "corona" is a process by which a current develops from an electrode with a high potential in a neutral fluid, usually air, by ionizing that fluid to create plasma around the electrode. The ions generated pass charge to nearby areas of lower potential or recombine to form neutral gas molecules. When the potential gradient is large enough at a point in the fluid, the fluid at that point ionizes and it becomes conductive. Air near the electrode can become ionized (partially conductive), while regions more distant do not. When the air becomes conductive, it has the effect of increasing the apparent size of the conductor region. Since the new conductive region is less sharp, the ionization will not extend past this local region. Outside of this region of ionization and conductivity, the charged particles slowly find their way to an oppositely charged object and are neutralized. The non-thermal plasma produced contains ROS that have a much higher reactivity than oxygen in the form of stable oxygen molecules. The ROS produced include atomic oxygen, singlet oxygen, hydrogen peroxide, superoxide anion, tri-atomic oxygen and hydroxyl radicals. The ROS attach themselves to the surfaces of pathogen at bond sites to create strong oxidizing radicals. These radicals draw out the hydrogen that is present in these contaminants breaking down the surface membranes and rendering them inactive. Species within the group of ROS have different half-lives. For example, it is known that hydrogen peroxide has a half-life of less than a second. This is in contrast to tri-atomic oxygen, i.e., ozone, for which studies and testing show that it can sustain a half-life up to 20 minutes, depending on the bio load within the treated area.

Figure 1:
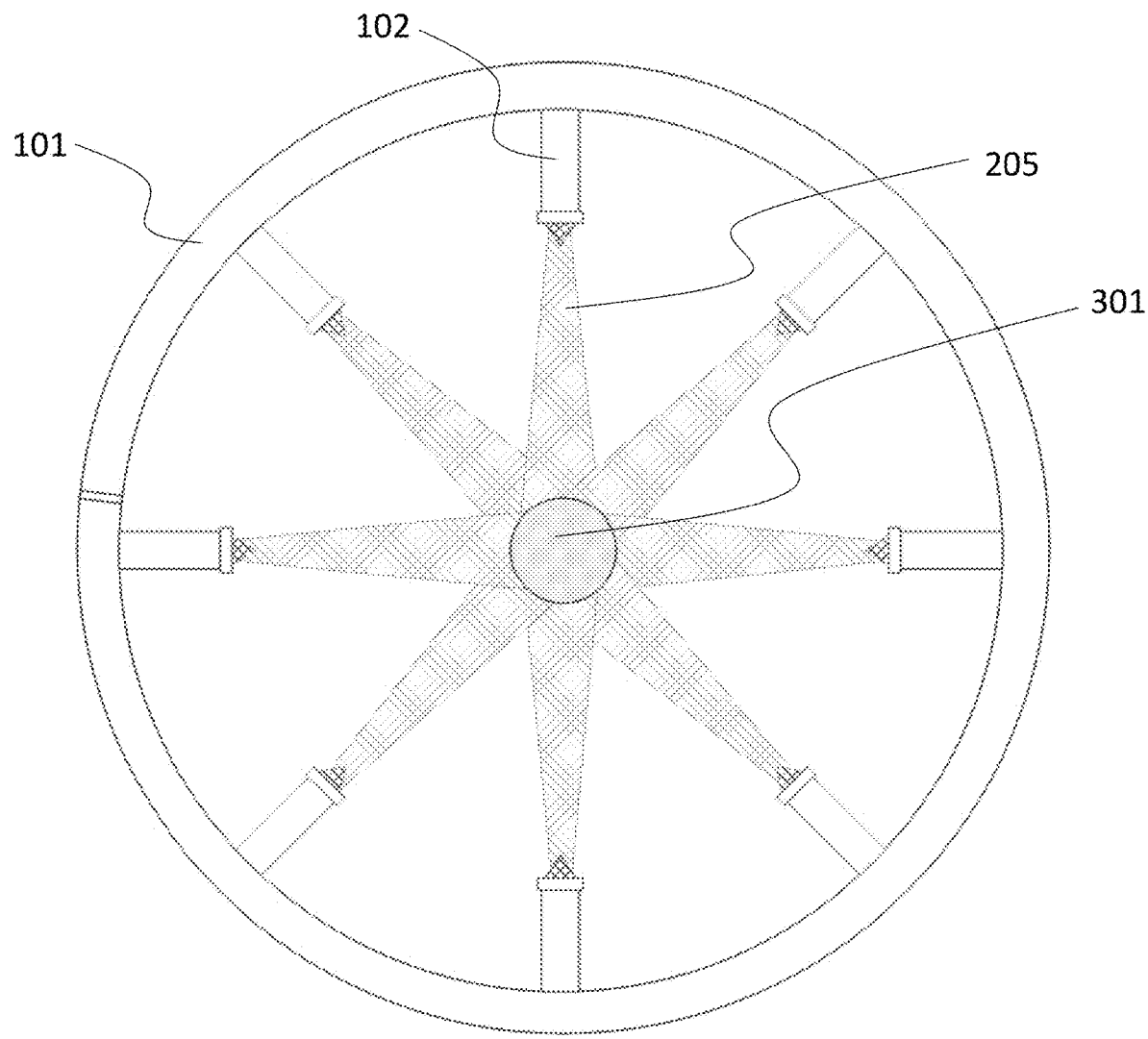
FIG. 1 depicts a portion of the interior of the reaction chamber including the anode rail assembly and the cathode rail which make up the reactor.

FIG. 1 depicts a partial interior view of an exemplary reaction chamber 500 from a top view (including the anode rail assembly 100 and the cathode rail assembly 300 which make up a reactor 200). The anode rail assembly 100 includes a helical anode rail 101, anode discharge elements 102, and an anode rail support 110 (shown in FIG. 3). The cathode rail assembly 300 comprises one or more cathode rails 301 (here only a single cathode rail is illustrated) and may be mounted using one or more cathode rail supports (not shown). As illustrated in FIG. 1, the anode rail assembly 100 and the cathode rail assembly 300 are separated by a hollow, cylindrical air gap (or space where plasma fields 205 can be generated). For illustration purposes, FIG. 1 shows the plasma fields 205 associated with the discharge anode elements for a single loop of the helix; in operation, however, a generally cylindrical plasma field may be formed by the plurality of discharge anode elements in the hollow, cylindrical air gap. When sufficient power is supplied to the reactor 200, individual fan-shaped non-thermal plasma fields 205 are generated which generate ROS when ambient air is passed through the plasma field.

In some embodiments, the reaction chamber 500 may contain a plurality of reactors 200. For example, there may be at least 2, 3, 4, 5, or 6 reactors 200 within a single reaction chamber 500, and each reactor may have a separate power supply. In one embodiment, for example, at least one reactor 200 is connected to a low voltage power supply at line frequency (60 Hz) and at least one other reactor 200 is connected to a high voltage power supply at a much higher frequency. In yet another embodiment, two or more of the plurality of reactors 200 are each connected to its own respective high voltage power supply to permit each individual reactor to be powered on or off individually. In this latter embodiment, the volume of production of ROS having longer half-lives can be varied simply by turning on or off additional reactors. By way of further example, if two reactors are both being operated using high voltage power supplies, one can reduce the volume of longer-half-life ROS (e.g., ozone) by half simply by turning off one of the two reactors.

Figure 2:
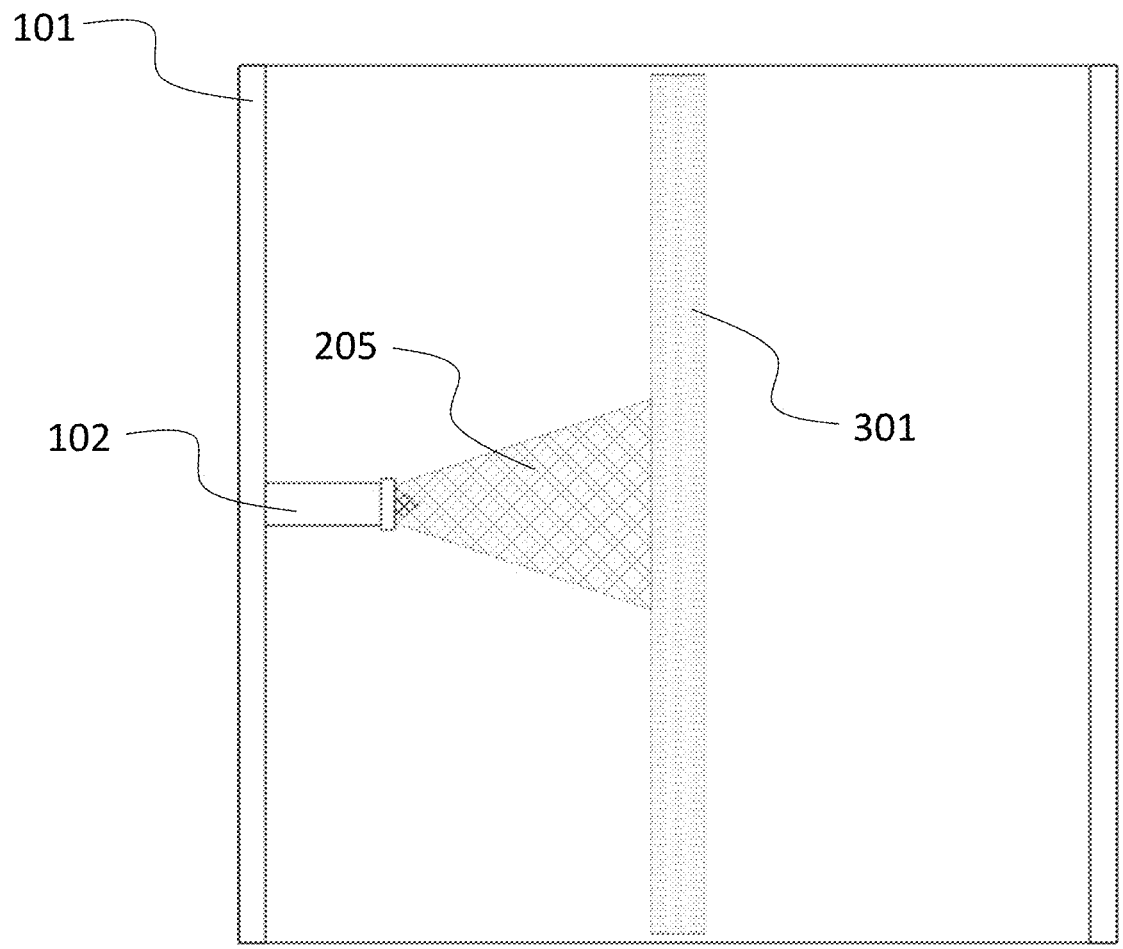
FIG. 2 generally depicts a fan-shaped non-thermal plasma field that can be generated using a single anode discharge element consistent with the reaction chamber of FIG. 1.

FIG. 2 generally depicts a fan-shaped non-thermal plasma field 205 that can be generated using a single, isolated anode discharge element 102 consistent with the reaction chamber of FIG. 1. FIG. 2 is a cross sectional view of the reaction chamber illustrated in FIG. 1, but it has been simplified to depict only a single anode discharge element.

Figure 3:
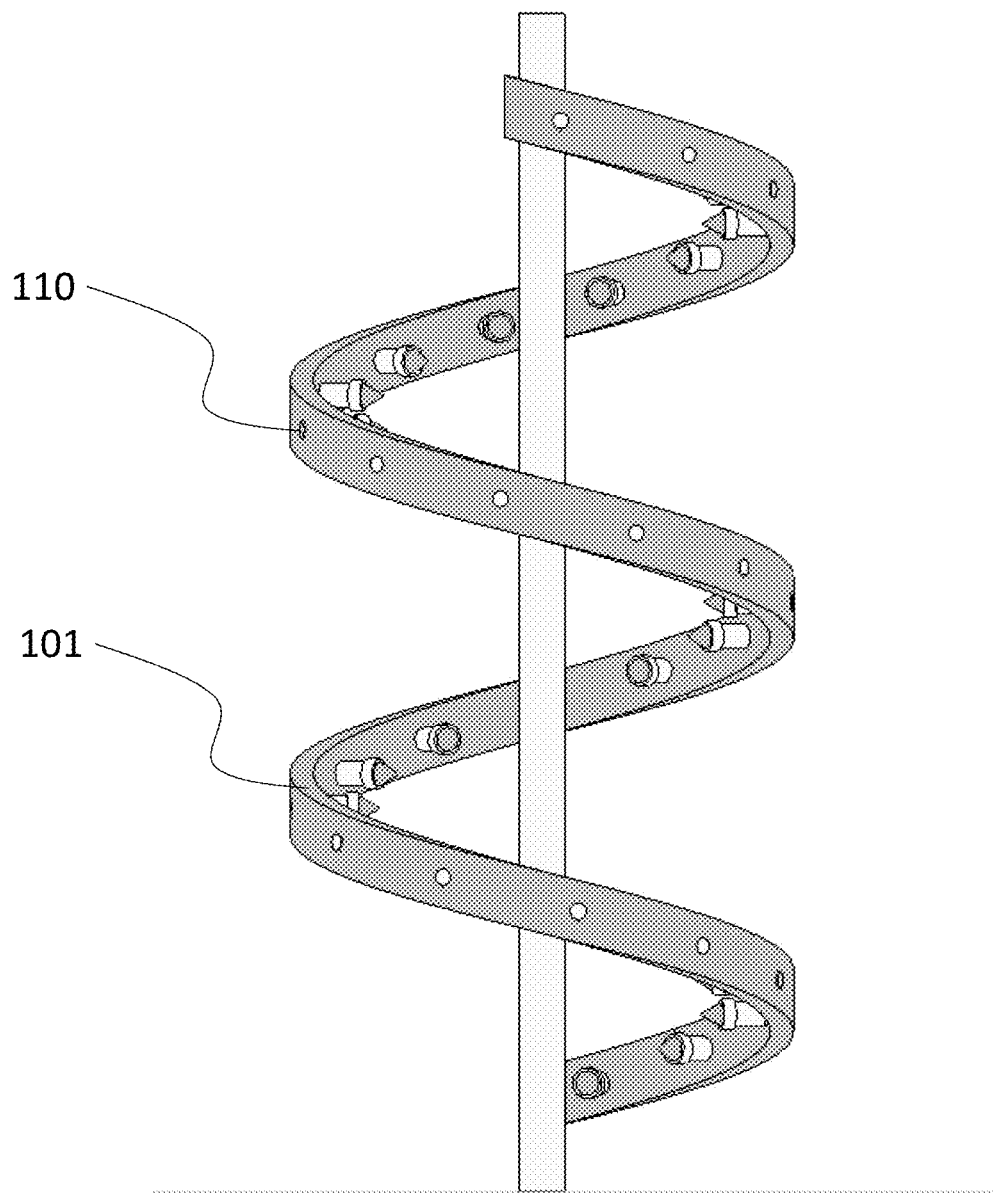
FIG. 3 illustrates some of the details of the anode rail assembly of FIG. 1

FIG. 3 illustrates the details of the anode rail assembly 100 of FIG. 1. The anode rail assembly 100 includes a helical anode rail 101 made of a first conductive material and has a longitudinal axis (not shown). The helical anode rail 101 has a plurality of discharge anode elements 102. Each of the discharge anode elements 102 has a proximal end and a distal end. The proximal ends of the discharge anode elements 102 can be permanently or removably secured to the helical anode rail 101. The anode rail assembly may be secured using connection studs 602 and nylon screw (not depicted) that affix the helical anode rail 101 to the anode rail support 110 via the mounting point 120. The anode rail support 110 is made of non-conductive material to isolate the anode rail from the other components of the reaction chamber. The connection studs 602 are preferably nylon in order to eliminate any cross connections.

Figure 4:
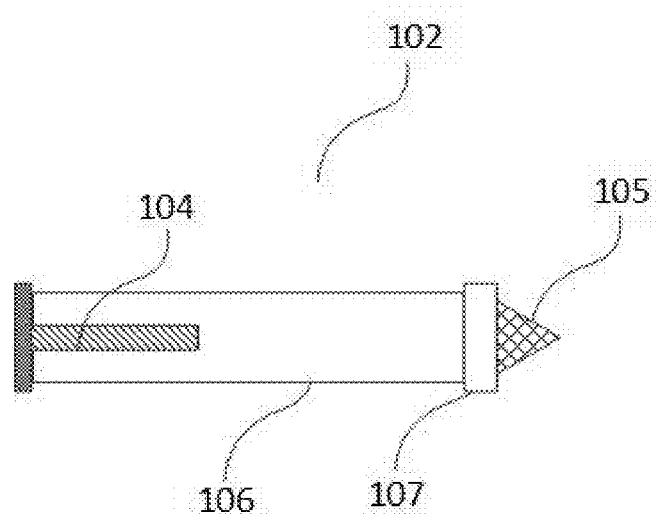
FIG. 4 is a close-up drawing illustrating the details of one of the plurality of discharge anode elements of the anode rail assembly of FIG. 1.

FIG. 4 is a close up drawing illustrating the details of one of the plurality of discharge anode elements 102 of the anode rail assembly of FIG. 1. The anode discharge element 102 has internal threads 104 located on one end to permit a conductive bolt to be connected the anode discharge element 102 to the helical anode rail 101. While the discharge anode element 102 can be formed as a unitary piece, it can also be milled as multiple parts and then assembled. For example, the tip 105 may be formed as part of, or be formed separately and then secured to, the anode discharge element 102. Tip 105 may be rounded or conical (as illustrated), and preferably, has a textured surface, such as a rough milled surface, for better conductivity. Another part of the discharge anode element 102 may be an isolation cup 107 to help control the gradient potential. The textured surface of the tip 105 can also comprise one or more of grooves, cross-hatching, etchings, ridges, dimplings, and pittings.

Figure 5:
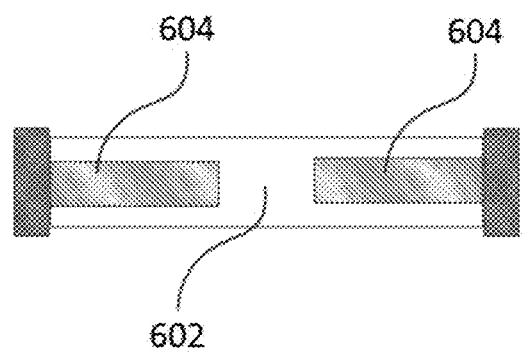
FIG. 5 is a close-up drawing illustrating the details of a connection stud for securing an anode rail or cathode rail to the reaction chamber.

FIG. 5 is an illustration of a connection stud 602. The anode rail may utilize at least one connection stud 602, and preferably, multiple connection studs 602. The connection stud 602 may have two sets of internal threads 604 located at each end of the connection stud 602. Connection studs similar in design to connection stud 602 may be used to mount both conductive rails (e.g. helical anode rail 101 and cathode rail 301) at one or more mounting points (e.g., mounting point 120 for the anode rail (see, e.g., FIG. 1). The rails are then secured through one or more support rails 210 using non-conductive screws (not depicted) which mate with the threads in the connection studs 602. Preferably, the screws and connection studs are made of nylon. The use of the nylon serves two requirements. One is that the screws are non-conductive and eliminate the ability to create a cross connection and/or short. The other is that the nylon material has the ability to withstand the ROS being created within the reaction chamber. Testing has shown that tri-atomic oxygen has the ability to break down rubber and some plastics, whereas nylon can withstand the effects of tri-atomic oxygen.

The cathode rail 301 is elongated and is substantially cylindrical, and may be about 1-3 inches wide and at least twice as long as wide. Preferably, the cathode rail is in the shape of a rod and at least a portion of an outer surface of the cathode rail 301 is textured (as described in detail elsewhere in this specification), which facilitates formation of a plasma field.

Figure 6:
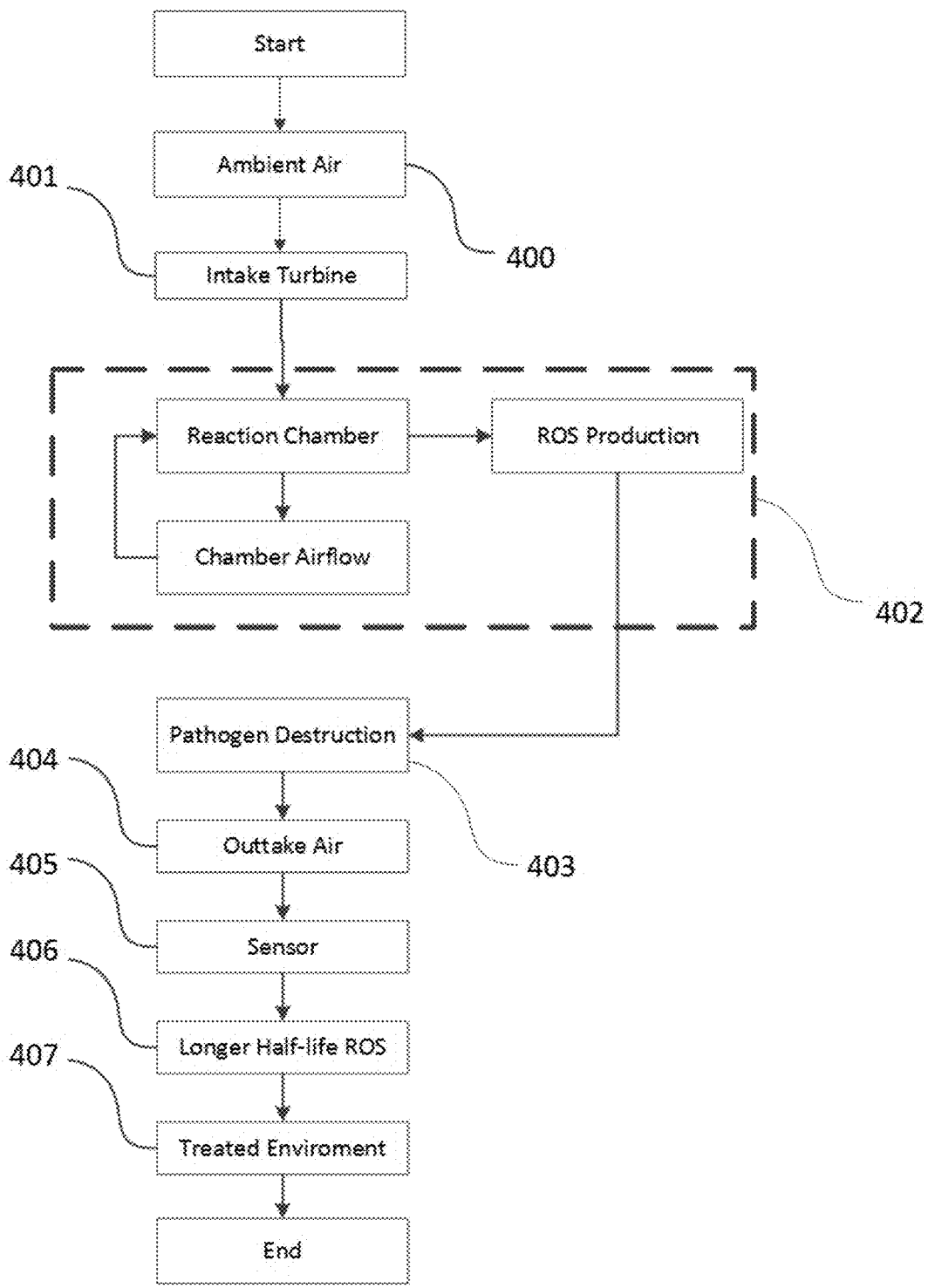
FIG. 6 is a block diagram illustrating different aspects of a process by which air can be treated using a plasma field generated in a reaction chamber.

FIG. 6 is a block diagram illustrating different aspects of a process by which air can be treated using a non-thermal plasma field generated in a reaction chamber. FIG. 6 outlines a process of the present invention where ambient air 400 is drawn into the reaction chamber process 402 with the use of an intake turbine in step 401 (which could utilize a blower in lieu of a turbine). Once in the reaction chamber, the oxygen molecules, through the production of non-thermal plasma, are converted into ROS as part of the reaction chamber process 402. Once created, the ROS attach themselves to the surfaces of pathogens at bond sites to create strong oxidizing radicals. These radicals draw out the hydrogen that is present in these contaminants breaking down the surface membranes and rendering them inactive, as part of pathogen destruction process 403. The treated air and some low residual species, mainly atomic oxygen, singlet oxygen, hydrogen peroxide, superoxide are then released as part of the outtake air process 404 into the treated environment in step 407. The process may optionally include a sensor step 405 to monitor ROS product from the reaction chamber process 402. Optionally, when producing certain ROS which have an extended half-life (e.g., a tri-atomic oxygen species with a half-life of 20 minutes), it may be preferable to use a catalytic filter (such as a manganese dioxide filter as discussed in greater detail below) to neutralize such tri-atomic oxygen species as part of optional step 406 prior to being released in the treated environment in step 407.

Figure 7:
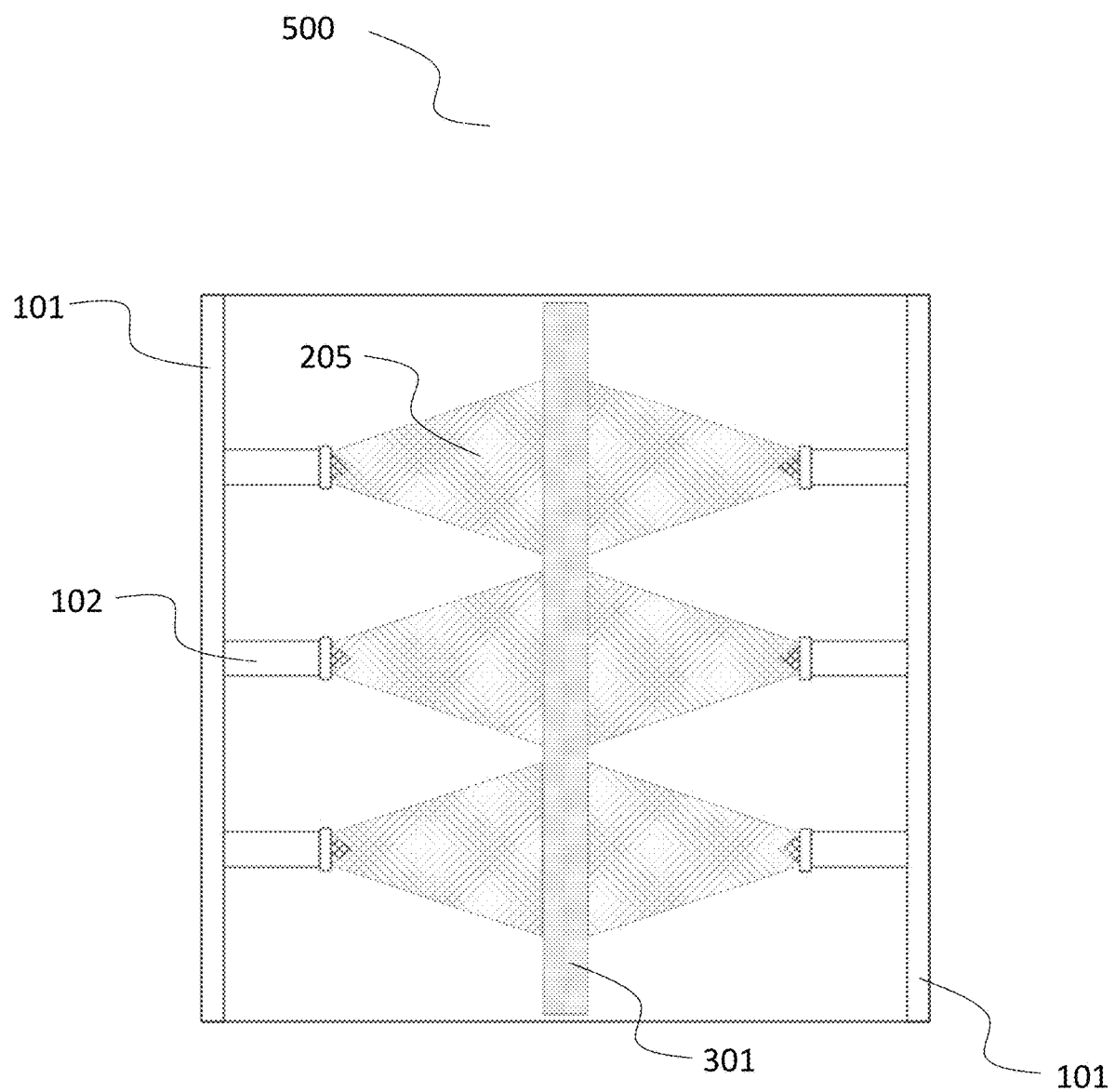
FIG. 7 depicts a cross sectional view of a reaction chamber having an anode rail assembly and cathode rail positioned such that the plurality of anode discharge elements face the cathode rail.

Referring now to FIG. 7, the reaction chamber 500 is constructed from a non-metallic chamber that houses a reactor 200. In a preferred embodiment, the chamber is round to promote improved airflow. The reactor 200 has two high voltage rails, one of which is a cathode rail assembly 300 and one that is the anode rail assembly 100. The cathode rail assembly 300 may be connected to a power supply, as described elsewhere herein. The anode rail assembly 100 is connected to the output of the same power supply. The two rails are separated by a hollow, cylindrical air gap where the non-thermal plasma 205 is produced. Each rail is attached the support structure with the use of nylon screws and non-conductive connection studs 602 in order to eliminate cross connections. In the embodiment shown in FIG. 7, the anode rail assembly 100 includes a rail (helical anode rail 101) that has multiple discharge points/receptors (e.g., anode discharge elements 102). Optionally, the cathode rail assembly 300 may have multiple discharge receptors 302 (not shown). During operation, a plasma field 205 is generated in the gap between the anode rail assembly 100 and the cathode rail assembly 300. One of skill in the art would appreciate that the gap is determined in part based on the magnitude of the voltage being used to create the plasma field. One of skill in the art would also appreciate that the size of the gap is also impacted by the conductive material of the helical anode rail 101 and the cathode rail 301. Preferably, the gap is less than a few inches, and more preferable, the gap is less than 1 inch. More preferably, the gap is less than about 0.75 inches. By way of examples, the anode assembly and the cathode rail may be separated by an air gap of approximately four inches (4") when applying a voltage level of 5,000 volts, by an air gap of about two inches (2") when applying a voltage level of 2,000 volts, and by an air gap of less than an inch when applying a voltage level of 1,000 volts. One of skill in the art would understand how to design and/or select a power supply that could be used with the inventions disclosed herein, including for example, using a power supply such as the OZ120WAC Ozone Power Supply by Chirk Industries, which can utilize either 95-125 VAC or 200-250 VAC and can provide power having 3-20 KV and a frequency of 10 KHz to 35 Khz.

In one embodiment the invention is an air treatment apparatus. The air treatment apparatus may have an intake portion and an output portion. The air treatment apparatus may also contain a reaction chamber located between the intake portion and output portion.

The reaction chamber may have an anode rail assembly. The anode rail assembly has an anode rail made of a first conductive material and has a longitudinal axis. The anode rail also has a plurality of discharge anode elements. Each of the plurality of discharge anode elements has a proximal end and a distal end. The proximal ends of the discharge anode elements can be permanently or removably secured to the anode rail. Each of the plurality of discharge anode elements is electrically coupled to each other and to the anode rail.

In some embodiments, the reaction chamber includes a cathode rail that is made of a second conductive material. The cathode rail can be a solid metal rod or it can comprise a plurality of metal elements electrically coupled to each other such that they collectively serve as a rail. Preferably the plurality of metal elements are spaced adjacently to each other so as to form a substantially continuous rail even though it may comprise multiple elements. An anode rail may be formed in the shape of a helix, with a plurality of discharge anode elements spaced along the helix. The cathode rail may be elongated and may be placed substantially along the longitudinal axis of the helical anode rail. The cathode rail is accordingly spaced from and generally faces the plurality of discharge anode elements. In one particular embodiment, the anode rail assembly and the cathode rail are located relative to each other so as to form a hollow, cylindrical space (or gap or void), wherein the space separates the cathode rail from the plurality of discharge anode elements such that the discharge anode elements do not cross the cylindrical space. The space permits a plasma field to be generated during operation, and preferably, the plasma field is a non-thermal plasma field. The space or gap permits air to be used as a dielectric and thus can advantageously avoid the use of a glass member. The radius and spacing of the turns in the helix is sized relative to the power level of the power supply. An exemplary helix is depicted in FIG. 3, in which the helical anode rail has approximately 2.5 turns such that each successive turn is spaced about 2 inches from the prior turn. Preferably, the cathode rail is cylindrical, for example, in the shape of a rod. Preferably, each of the plurality of discharge anode elements on the helical anode rail is spaced a fixed distance from a neighboring discharge anode. One of skill in the art who uses the would understand that if the anode discharge elements are placed too close together, any contaminants in the air (e.g., dust) could cause arcing. Accordingly, the anode discharge elements must be spaced sufficiently apart to minimize the likelihood of arcing but sufficiently close to promote plasma generation. Preferably, the spacing between the discharge anode elements is fixed between approximately ⅛ inch and approximately 3 inches.

Figure 8:
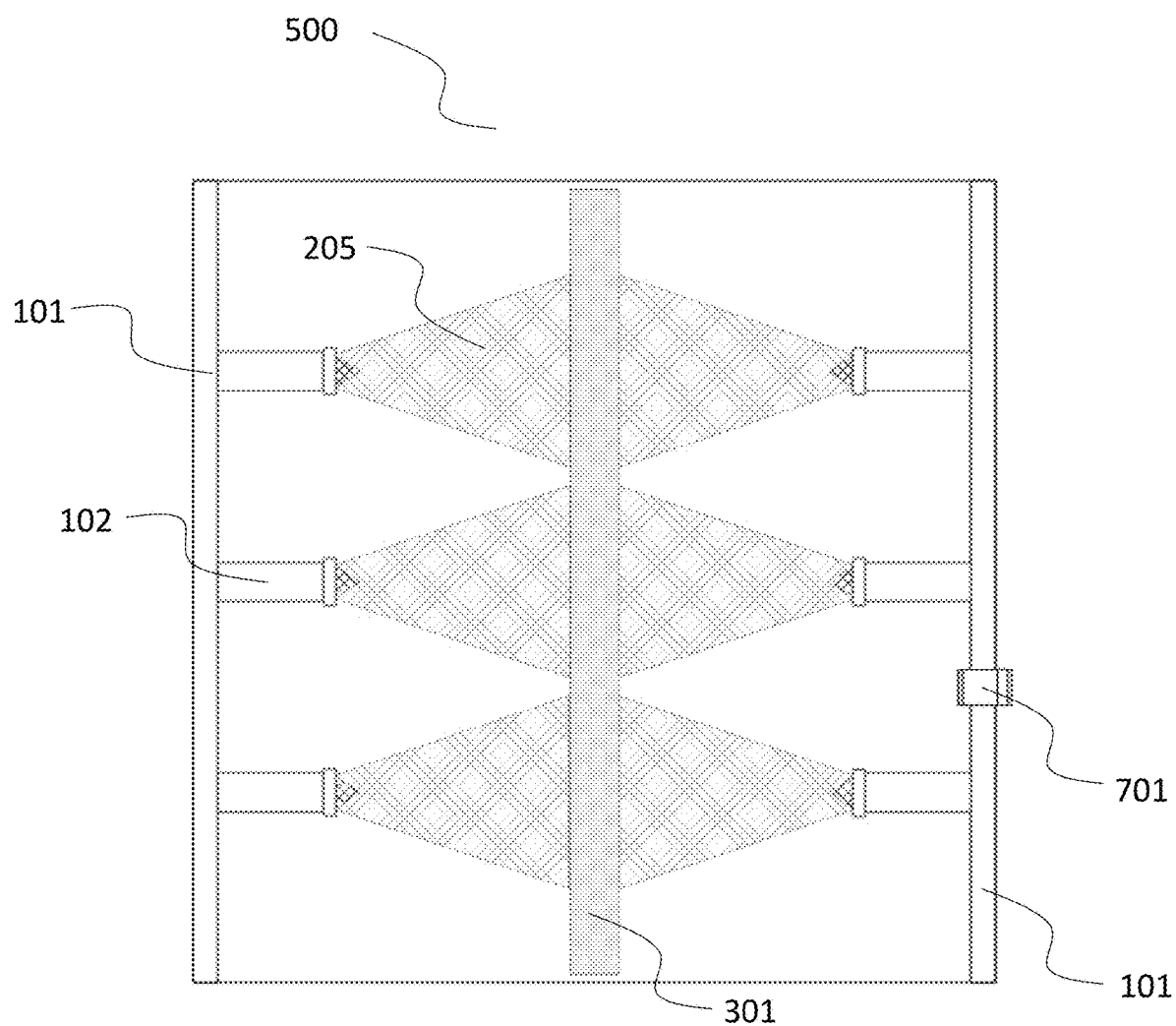
FIG. 8 depicts a cross sectional view of a reaction chamber indicating a location of a sensor in one embodiment of the present invention.

Optionally, the apparatus of the present invention may include a performance monitor that includes one or more power supply sensors to measure the electrical consumption characteristics of the power supply being used to generate a plasma field (e.g., amperage being used by the power supply, voltage level of the power supply, overall energy or power consumed by the power supply). The performance monitor may include, in addition to or in lieu of the power supply sensors, one or more light sensors to measure the optical characteristics of the plasma field. A plasma field produces light having certain spectral characteristics, which can be monitored using fiber optic technology and a receiver (e.g., an LED receiver). While one optical sensor 701 may be used in the mid-section of the helix as illustrated in FIG. 8 to monitor the core of the plasma field, preferably, a plurality of optical sensors spaced around the perimeter of the plasma generating stage, and more preferably spaced throughout the cylindrical perimeter of the plasma generating stage. An ideal plasma field that is generated by the apparatus may be assessed and characterized such that if the plasma begins to generate light having a spectrum beyond the spectrum previously determined for an ideal plasma field (e.g., a predetermined set of spectral characteristics), then this optical information may be used to warn the operator (e.g., using a visual warning) or to shut down the device. The assessments may be conducted at the manufacturing facility and stored in the memory of the device, and alternatively, the assessments may be conducted on the job site and stored in the device. Optionally, the optical information can be utilized in conjunction with the power supply sensor, which separately monitors the electrical consumption characteristics of the power supply, for example, to determine a likelihood that arcing is occurring, for example, which may be deduced from the fact that the amperage being consumed exceeds a predetermined current threshold; in such an event, the performance monitor can cause the apparatus to be shut down to minimize concerns that the device is operating less than optimally. The performance monitor can include one or more comparator that compares in real time the spectral characteristics of the plasma field to at least one set of predetermined spectral characteristics and/or that compares in real time the electrical consumption characteristics of the power supply to at least one set of predetermined electrical consumption characteristics. Preferably, the light monitor is programmable to permit an alarm to be triggered if the spectral characteristics of the plasma field deviates from the at least one set of predetermined spectral characteristics by more than a first threshold. More preferably, the light monitor is programmable to permit an alarm to be triggered if the electrical consumption characteristics of the power supply deviates from the at least one set of predetermined electrical consumption characteristics by more than a second threshold. More preferably, the light monitor is programmable to permit an alarm to be triggered only if a) the spectral characteristics of the plasma field deviates from the at least one set of predetermined spectral characteristics by more than a first threshold; and b) the electrical consumption characteristics of the power supply deviates from the at least one set of predetermined electrical consumption characteristics by more than a second threshold.

In alternative embodiments, the apparatus may include a cathode rail assembly that comprises a rail and a plurality of cathode elements extending from the rail. Each of the plurality of cathode elements has a proximal end and a distal end. The proximal ends of the cathode elements can be permanently or removably secured to the cathode rail, and each of the plurality of cathode elements is electrically coupled to each other and to the cathode rail. When the cathode rail assembly is opposite the anode rail assembly, the distal ends of the cathode elements generally face the distal ends of the discharge anode elements. The cathode elements may be placed directly opposite the discharge anode elements; preferably, however, the cathode elements are spaced such that each of the cathode elements is spaced equally distant from the two closest discharge anode elements to facilitate the generation of a plasma field in the space between the anode rail assembly and the cathode rail assembly. The cathode rail has an outer surface, and preferably, at least a portion of the outer surface is textured. In some embodiments, the middle of the outer surface is textured. One of skill in the art would appreciate that the width and length of the cathode rail, as well as the width and length of the anode rail, can be adjusted to meet the specific needs of the treatment application, and appreciate further that longer lengths may require higher-wattage power supplies. In some embodiments the cathode rail is at least about 1, 2, or 3 inches wide and is at least about 8, 9, 10, 11, 12, 13, or 14 inches long. In some embodiments the anode rail assembly is at least about 1, 2, or 3 inches wide and is at least about 6, 7, 8, 9, or 10 inches long when measured along the central longitudinal axis of the helix. Preferably, the anode rail assembly is about the same or shorter in length than the length of the cathode rail (when measured along the central longitudinal axis of the helix). Similarly, one of skill in the art would appreciate that the number of turns of the helix of the anode rail can be adjusted to meet the specific needs of the treatment application. While any number of turns may be used, preferably the helix is formed to have at least two turns, and preferably more than about six turns. Similarly, one of skill in the art would appreciate that the spacing of adjacent turns of the helix can be adjusted to meet the specific needs of the treatment application. Preferably, successive turns of the helix should be spaced such that the rail is spaced between about one inch and about three inches; tighter spacings have a potential for arcing whereas more distant spacings can introduce non-uniformities in the plasma field. By way of example, a helical anode that has about six turns and an overall longitudinal length of 12 inches would result in a spacing of about 2 inches between adjacent portions of the anode. Preferably, the textured surface of the cathode rail faces the distal ends of the discharge anode elements. The textured surface of the cathode rail may comprise one or more of grooves, cross-hatching, etchings, ridges, dimplings, and pittings.

While in many of the embodiments described above, the reaction chamber is described as having a helical anode rail and an elongated cathode rail located along the axis of the helix, the reaction chambers could, in the alternative, be configured to utilize a helical cathode rail and an elongated anode rail located along the axis of the helix, along with an alternating current power supply. Accordingly, the present invention encompasses a helical rail that serves as an anode, surrounding a centrally-located, elongated rail (that serves as a cathode), as well as a helical rail that serves as a cathode, surrounding a centrally-located, elongated rail (that serves as an anode). The descriptions herein relating to the physical characteristics of a helical anode would be applicable to a helical rail that functions as a cathode. For example, a helical rail (regardless of whether it functions as an anode or a cathode) may include protruding elements (e.g., a plurality of discharge anode elements along a helical anode rail; or a plurality of cathode elements along a helical cathode rail), and such protruding elements may have tips that include a textured surface, comprising one or more of grooves, cross-hatching, etchings, ridges, dimplings, and pittings.

The air treatment apparatus of the embodiments discussed above may also have an intake blower located in the intake portion. The intake blower is configured to draw air into the reaction chamber. The blower may be adjustable to control the flow rate of air through the reaction chamber. For example, when using a low voltage power supply and/or when generating ROS with very short half-lives, an airflow rate of 60-70 CFM may be sufficient. When using a high voltage / high frequency power supply (which generates a greater volume of ROS with longer half-lives), a higher air flow rate, for example, 120-200 CFM, may be more desirable to treat air and contaminants outside of the reaction chamber. Such a configuration would be preferred in environments where there is a need to treat surrounding air and surfaces, such as in an unoccupied hospital room in between surgeries. In addition, using different intake blowers may be useful in treating different sized areas. For example, a 120 CFM blower can increase airflow through a reactor which then increases the ability of the reactor to circulate more ROS in any given time. Any number of blower fans on the market could be used, including for example, the Fantech FR100, FR110, FR125, FR140, FR200, and FR250 models. One of skill in the art would select a blower fan based on the environment in which a treatment apparatus is being place or is expected to be used.

In alternative embodiments, however, the air treatment apparatus may be placed in an existing duct or other air flow where by the air is forced to flow through the reaction chamber which will obviate the need for an intake blower being incorporated into the air treatment apparatus.

The air treatment apparatus may include power supply circuitry capable of delivering sufficient energy to generate a non-thermal plasma field in the space between the anode rail assembly and the cathode rail, or between the anode rail assembly and the cathode rail assembly in those alternative embodiments having the cathode rail assembly. The power supply circuitry may comprise a line voltage power supply (using standard household AC (e.g., 60 Hz, 120 VAC to generate a 1,000 VAC at 60 Hz)) to create a non-thermal plasma field having a first set of characteristics (e.g., a production of different ROS that includes a substantial volume of highly reactive species having relatively short half-lives (e.g., less than 1 second)). The voltage may be applied to the anode, and the cathode shares a common ground with the power supply. The power supply may utilize a transformer or other known circuitry to deliver energy at frequencies and voltages higher than those associated with standard household AC in order to create a non-thermal plasma field having ROS with a second set of characteristics, which are different from those generated using standard AC power (e.g., a production of different ROS that includes a substantial volume of less-reactive species having relatively long half-lives (e.g., greater than 1 minute). For example, through testing it has been learned that high voltages, e.g., greater than about 1,000 VAC at a frequency of greater than about 1,000 Hz, produce greater volumes of ROS having longer half-lives than the volumes of such ROS generated using lower voltages and frequencies, e.g., 120 VAC at 60 Hz to generate 1,000-5,000 VAC at about 60 Hz. (For purposes of this application, it should be understood that the references to frequencies greater than line frequency are intended to refer to frequency "under load"—in other words, the frequency as would appear during operation at the anode rail.). In other embodiments the power supply operates using greater than about 2,000 VAC at a frequency of greater than about 10,000 Hz. In yet other embodiments the power supply operates using greater than about 4,000 VAC at a frequency of greater than about 15,000 Hz. In additional embodiments the power supply operates using greater than about 5,000 VAC at a frequency of greater than about 10,000 Hz. The high-frequency power is non-fluctuating. One of skill in the art would understand that a variety of power supplies having different voltage levels and operating frequencies could be used with the present inventions. One of skill in the art would select an appropriate power supply based upon the environmental conditions in which the apparatus is being used, or based upon the expected application of the apparatus. For example, where it is desired to neutralize pathogens in air, a lower voltage power supply with a lower frequency may be more desirable because ROS with short half-lives can be effectively used to interact with pathogens in the air. On the other hand, where it is desired to treat a larger space, including by neutralizing pathogens that may be on nearby surfaces, the present invention would generate ROS having longer half-lives, and thus a higher voltage, higher frequency power supply may be preferred.

In some embodiments, the reaction chamber 500 may contains a "split core"—which is characterized by the reaction chamber 500 having a plurality of reactors 200, each of which reactor can be coupled to an independent power supply. Preferably at least one reactor 200 is connected to a low voltage power supply having standard line frequency (around 60 Hz) and at least one reactor 200 is connected to a high voltage power supply having a much higher frequency (e.g., more than ten times, more than 100 times); more preferably the voltage of the high voltage supply(ies) is much greater than the voltage of the low voltage power supply. Preferably, each of the plurality of reactors 200 is electrically isolated from the other reactors 200 to reduce the likelihood of electrical interference between the plasma fields. A surprising and unexpected benefit of the "split core" is that the low voltage power supply generates a greater volume of ROS that are highly reactive, such as singlet oxygen species and hydrogen peroxide, but have relatively short half-lives, while the high voltage power supply generates a greater volume of ROS which are less reactive but which have a longer half-lives (this would include, for example, ROS such as ozone). Thus, depending on the environment to be treated, one could selectively produce greater volumes of reactive species having either short half-lives or long half-lives by using a split-core and selectively operating a low voltage power supply and a high voltage power supply. Moreover, as is evident from this unexpected result and from other discussions herein, by using multiple reactors each having a low voltage power supply, one can selectively produce a greater or lesser volume of highly reactive species having relatively short half-lives by selectively turning on or off each of the low voltage power supplies. Similarly, by using multiple reactors each having a high voltage power supply, one can selectively produce a greater or lesser volume of less reactive species having relatively long half-lives by selectively turning on or off each of the high voltage power supplies.

The split core design permits a first power supply to be applied to the first reactor 200, and a second power supply to be applied to the second reactor 200. In some embodiments the amount of power supplied to each reactor 200 is the same, but with the split core, it is possible for the first and second reactors 200 to have entirely different power supplies. While the reactors 200 are electrically isolated from each other, preferably they are spaced near each other. Preferably, they are spaced in line with each other. For example, the first reactor 200 and the second reactor 200 may be aligned along a common axis.

In some embodiments the air treatment apparatus may include a sensor configured to monitor ROS levels in the area of the air treatment apparatus. Preferably the sensor is located externally to the apparatus. The sensor may have a programmable controllable link to the reaction chamber to control the reaction chamber based on collected data received from and/or concentration levels measured by the sensor, thereby permitting a feedback control loop to optimize performance of the air treatment device. The feedback from the sensor can be used, for example to adjust output levels and on/off control of the reaction chamber. In one embodiment, the sensor may be a heated metal oxide semiconductor (HMOS) sensor for tri-atomic oxygen that works by heating a substrate to a high temperature (around 300° F.). At this temperature, the substrate is very sensitive to tri-atomic oxygen. The sensor detects the level of tri-atomic oxygen by measuring the resistance across the substrate. The data from the sensor is then converted into a parts-per-million measurement (PPM) for tri-atomic oxygen. The programmable controllable link may be a programmable logic controller used to monitor the data from the sensor to control the voltage level supplied to the reaction chamber, or turn on or off, one or more reactors in order to control the volume of tri-atomic oxygen being produced. The sensor and the programmable controllable link may communicate wirelessly, for example, using Bluetooth or a Wi-Fi connection such as the 802.11 standard, and variations thereof. One of skill in the art would also appreciate that other controllers could be used, including for example, a microprocessor programmed to monitor measurements and respond to the measurements by adjusting the power supply and/or switching to a different, power supply. In a "split core" reaction chamber 500 having a plurality of reactors each having a high voltage power supply, the programmable link may turn off one or more high voltage power supplies when ozone levels reach a predetermined threshold in the external environment. Moreover, in certain embodiment which include reaction chambers using low voltage power supplies, it may be desirable to continue to power one or more of the low voltage power supplies even after turning off the reactors using high voltage power supplies.

The first conductive material of the cathode may be different from the second conductive material of the anode; preferably, however, the first conductive material is the same as the second conductive material. Preferably, the first and second conductive materials are highly conductive. For example, the first conductive material and second conductive material may each be silver, copper, gold, aluminum, zinc, brass, steel, or stainless steel, as well as alloys of the foregoing materials. The stainless steel may be, for example, 200 Series such as 201 or 202, 300 Series such as 304 or 316, ferritic stainless steel, martensitic stainless steel, superaustentic stainless steel, or duplex stainless steel. In addition, the discharge anode elements may be made of a conductive material that is different from the conductive material of the anode rail.

In variations of the embodiments discussed above, at least a portion of an outer surface of the distal ends of the discharge anode elements is textured to facilitate the discharge of electrical energy, thereby enhancing the generation of non-thermal plasma. The textured surface of the distal ends of the discharge anode elements may have one or more of grooves, cross-hatching, etchings, ridges, dimplings, and pittings. The distal ends of the discharge anode elements may also be shaped to form a tip, such as a rounded dome or a conical tip (as illustrated in FIG. 2).

The air treatment apparatus may also have one or more filters. For example, the apparatus may include a manganese dioxide honeycomb filter located on the discharge side of the device. In this embodiment, the filter acts as a catalyst in order to neutralize tri-atomic oxygen in the discharged air when needed. Optionally, an additional filter may be located on the intake side of the device, including, for example, a 30 PPI filter. When placed on the intake side, the filter keeps dust out of the reaction chamber. Optionally, other catalytic filters known to those skilled in the art could be utilized on the discharge side, which could be used in lieu of an exhaust filter.

The anode rails functions as a common electrical bus and may be electrically coupled to a plurality of discharge anode elements extending outward from the anode rail toward a cathode rail.

In some embodiments, the anode assembly is an elongated helix and has a distance of D measured along a longitudinal axis of the helix. The cathode assembly may be elongated, may be substantially cylindrical, and may have a distance of less than or about D. The plurality of discharge anode elements may extend inwardly of the helix towards the cathode assembly but remain spaced from the cathode assembly to permit the creation of a non-thermal plasma field in the cylindrical space there between.

The various embodiments of the apparatus above may be used to perform methods of generating ROS and non-drifting non-thermal plasma fields. The methods comprise drawing air into a reaction chamber of any of the embodiments described above, supplying energy to the anode rail assembly and the cathodes (whether cathode rails or cathode rail assemblies) to generate a non-thermal plasma field in the space between such anodes and cathodes, and causing the air to flow through the plasma field created in the reaction chamber.

The non-thermal plasma field created using such methods may be created using about 120 VAC at a frequency of about 60 Hz which is transformed to about 1,000-5,000 VAC at a frequency of about 60 Hz. In other embodiments the non-thermal plasma field is created using greater than about 1,000 VAC at a frequency of greater than about 1,000 Hz. In yet other embodiments the non-thermal plasma field is created using greater than about 2,000 VAC at a frequency of greater than about 10,000 Hz. In yet other embodiments the non-thermal plasma field is created using greater than about 4,000 VAC at a frequency of greater than about 15,000 Hz. Preferably, energy of a magnitude and frequency is used to create a non-thermal plasma field that is preferably substantially homogenous throughout the gap. The energy may be used to generate a fan-shaped non-thermal plasma field that emanates from one or more of the plurality of discharge anode elements towards the cathode rail.

The ROS created would include but not be limited to atomic oxygen, singlet oxygen, hydrogen peroxide, superoxide anion, tri-atomic oxygen and hydroxyl radicals.

The embodiments described herein can also optionally include a catalytic filter to reduce and or neutralize unwanted Tri-Atomic Oxygen (for example, through the use of a honeycomb manganese dioxide filter). In such a filter, manganese dioxide or other similar reactive material may be heated to a high temperature (e.g., 400° F.) which serves as a catalyst to break down ozone. Such a filter may be desirable for use, for example, in environments where ozone is generally undesirable (e.g., in a hospital room during a patient's operation). If desirable, the reaction chamber could be configured to permit treated air to bypass such a filter altogether, and alternatively to exit through the honeycomb filter for reduction of certain ROS. Such a configuration could be achieved using airflow controls, for example, by using a controllable manifold (e.g., 1:2 manifold that can direct airflow through the honeycomb filter or by-pass it the filter) or by using an adjustable Y-valve.

The foregoing and other aspects, features, details, utilities, and advantages of the present invention will be apparent from reading the following description and claims, and from reviewing the accompanying drawings. Those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An air treatment apparatus comprising:
   an intake portion and an output portion;
   a reaction chamber located between the intake portion and output portion,
   wherein the reaction chamber comprises:
   an anode rail assembly comprising:
   an anode rail made of a first conductive material and having a shape of a helix about a longitudinal axis, and
   a plurality of discharge anode elements, wherein each of the plurality of discharge anode elements has a proximal end and a distal end, the proximal ends of the discharge anode elements are secured to the anode rail, and the anode rail, and the distal ends comprise a distal tip and an element that helps isolate the gradient potential on the distal tip
   each of the plurality of discharge anode elements are electrically coupled to each other and to the anode rail;
   a cathode rail comprising a second conductive material, wherein the cathode rail is positioned along the longitudinal axis of the helical anode; and
   the anode rail assembly and the cathode rail being located relative to each other so as to form a cylindrical space, wherein the space separates the cathode rail from the plurality of discharge anode elements such that the discharge anode elements do not cross the cylindrical space;
   an intake blower located in the intake portion, wherein the intake blower is configured to draw air into the reaction chamber; and
   an alternating current power supply that is coupled to both the anode rail and the cathode rail, wherein the alternating current power supply delivers sufficient energy to generate a non-thermal plasma field in the space between the anode rail assembly and the cathode rail.

2. The air treatment apparatus of claim 1, further comprising a sensor configured to monitor tri-atomic oxygen, wherein the sensor is located externally to the apparatus.

3. The air treatment apparatus of claim 1, wherein the first conductive material is the same as the second conductive material.

4. The air treatment apparatus of claim 1, wherein the first conductive material is different from the second conductive material.

5. The air treatment apparatus of claim 1, wherein at least a portion of an outer surface of the distal ends of the discharge anode elements is textured.

6. The air treatment apparatus of claim 5, wherein the textured surface of the discharge anode elements comprises one or more of grooves, etchings, ridges, dimplings, and pittings.

7. The air treatment apparatus of claim 1, wherein the apparatus further comprises at least one filter.

8. The air treatment apparatus of claim 1, wherein the cathode rail is cylindrical.

9. The air treatment apparatus of claim 1, wherein each of the plurality of discharge anode elements is spaced a fixed distance from a neighboring discharge anode element.

10. The air treatment apparatus of claim 9, wherein the distance is fixed between approximately ⅛ inch and approximately 3 inches.

11. The air treatment apparatus of claim 1, further comprising a performance monitor, said performance monitor comprising:
one or more light sensors that monitor the optical characteristics of a plasma field that is generated in the space between the anode rail assembly and the cathode rail,
an optical receiver that analyzes the spectral characteristics of the generated plasma field;
a comparator that compares the analyzed spectral characteristics of the generated plasma field to a predetermined set of spectral characteristics and issues an alarm when at least a first condiction is met, said first condition being that the analyzed spectral characteristics deviates by more than a first predetermined minimum threshold from the predetermined set of spectral characteristics.

12. The air treatment apparatus of claim 11, wherein the performance monitor further comprises a power supply sensor that analyzes the electrical consumption characteristics of the power supply being used to generate the plasma field, wherein the comparator issues an alarm when at least the first condition is met and a second condition is met, said second condition being that the analyzed electrical consumption characteristics deviates by more than a second predetermined minimum threshold from a predetermined set of electrical consumption characteristics.

13. An ambient air treatment device, comprising:
a reaction chamber comprising:
an anode assembly and a cathode rail;
said anode assembly having a common electrical bus in the shape of a helix about a longitudinal axis and a plurality of discharge anode elements extending outward from the common electrical bus, said discharge anode elements having a textured surface on a distal end and an isolation portion configured to isolate the gradient potential on the textured surface;
said cathode rail comprising one or more conductive elements placed in electrical contact with each other so as to form an electrically-conductive, elongated cathode that is positioned along the longitudinal axis of the helical common electrical bus of the anode assembly;
wherein said anode assembly and said cathode rail are positioned in relationship to each other so as to form a cylindrical space that separates the cathode rail from the plurality of discharge anode elements such that the discharge anode elements do not cross the cylindrical space;
an airflow input on a first side of the anode assembly and the cathode rail; and
an airflow output on a second side of the anode assembly and the cathode rail; and
an alternating current power supply that is coupled to the anode assembly and to the cathode rail, wherein the alternating current power supply generates a plasma field between the anode assembly and the cathode rail.

14. The ambient air treatment device of claim 13, wherein the cathode rail is cylindrical.

15. The air treatment apparatus of claim 13, wherein each of the plurality of discharge anode elements is spaced a fixed distance from a neighboring discharge anode element.

16. The air treatment apparatus of claim 15, wherein the distance is fixed between approximately ⅛ inch and approximately 3 inches.

17. A method of generating a plasma field comprising:
drawing air into a reaction chamber, wherein the reaction chamber comprises:
an anode rail assembly comprising:
an anode rail made of a first conductive material and having a shape of a helix about a longitudinal axis, and a plurality of discharge anode elements, wherein each of the plurality of discharge anode elements has a proximal end and a distal end,
the proximal ends of the discharge anode elements are secured to the anode rail, and the distal ends comprise a distal tip and an element that helps isolate the gradient potential on the distal tip
each of the plurality of discharge anode elements are electrically coupled to each other and to the anode rail;
a cathode rail comprising a second conductive material, wherein the cathode rail is positioned substantially along the longitudinal axis of the helical anode rail;
an alternating current power supply coupled to the anode rail and to the cathode rail; and
a cylindrical gap located between the anode rail assembly and the cathode rail, wherein the gap separates the cathode rail from the plurality of discharge anode elements such that the discharge anode elements do not cross the cylindrical gap;
supplying energy using the alternating current power supply to generate a plasma field in the gap between the anode rail assembly and the cathode rail; and
causing the air to flow through the plasma field created in the reaction chamber.

18. The method of claim 17, wherein the plasma field is generated using greater than about 1,000 VAC at a frequency of about 60 Hz.

19. The method of claim 17, wherein the plasma field is generated using greater than about 1,000 VAC at a frequency of greater than about 1,000 Hz.

20. The method of claim 17, wherein the plasma field is generated using greater than about 2,000 VAC at a frequency of greater than about 10,000 Hz.

21. The method of claim 17, wherein the plasma field generated is substantially homogenous throughout the gap.

22. The method of claim 17, wherein the energy is used to create a cylindrical-shaped non-thermal plasma field.

23. The method of claim 17, wherein the plasma field is generated using the helical anode rail upon which each of the plurality of discharge anode elements is spaced a fixed distance from a neighboring discharge anode element.

24. The method of claim 17, wherein the plasma field generated is non-drifting.

25. The method of generating a plasma field of claim 17, further comprising:
measuring the optical characteristics of a plasma field that is generated;
comparing the measured optical characteristics of the generated plasma field with at least one set of predetermined optical characteristics and issuing an alarm when at least a first condiction is met, said first condition being that the measured optical characteristics deviates by more than a first predetermined minimum threshold from the at least one set of predetermined optical characteristics.

26. The method of generating a plasma field of claim 25, further comprising:

measuring the electrical consumption characteristics of the power supply being used to generate the plasma field;

and wherein the comparing step comprises:

comparing the measured electrical consumption characteristics of the power supply being used to generate the plasma field with at least one set of predetermined electrical consumption characteristics;

comparing the measured optical characteristics of the generated plasma field with at least one set of predetermined optical characteristics; and issuing an alarm when a) the measured optical characteristics deviate by more than a first predetermined minimum threshold from the at least one set of predetermined optical characteristics; and b) the measured electrical consumption characteristics deviate by more than a second predetermined minimum threshold from the at least one set of predetermined electrical consumption characteristics.

27. The air treatment apparatus of claim 1 wherein the alternating current power supply generates the plasma field using a frequency greater than 10,000 Hz.

28. The air treatment apparatus of claim 27 wherein the alternating current power supply generates the plasma field using a frequency less than 30,000 Hz.

* * * * *